United States Patent [19]

Beck et al.

[11] Patent Number: 4,954,437

[45] Date of Patent: Sep. 4, 1990

[54] CELL ENCODING RECOMBINANT HUMAN ERYTHROPOIETIN

[75] Inventors: Anton K. Beck, Wellesley; Raymond M. Withy; James R. Zabrecky, both of Framingham; Nicholas C. Masiello, Milford, all of Mass.

[73] Assignee: Integrated Genetics, Inc., Framingham, Mass.

[21] Appl. No.: 907,369

[22] Filed: Sep. 15, 1986

[51] Int. Cl.$^5$ .................... C12P 21/02; C12N 15/00; C12N 5/00; C07K 13/00
[52] U.S. Cl. ................... 435/69.4; 435/172.3; 435/240.2; 350/399; 935/13
[58] Field of Search ............ 435/240.2, 70, 172.3

[56] References Cited

U.S. PATENT DOCUMENTS

| 4,377,513 | 3/1983 | Sugimoto et al. ............. 26/112 R |
| 4,419,446 | 12/1983 | Howley et al. ................ 435/68 |
| 4,465,624 | 8/1984 | Chiba et al. ................. 260/112 R |
| 4,677,195 | 6/1987 | Hewick et al. . |
| 4,703,008 | 10/1987 | Lin ............................. 435/9 |

FOREIGN PATENT DOCUMENTS

| 0236059 | 9/1987 | European Pat. Off. . |
| 8502610 | 6/1985 | PCT Int'l Appl. . |
| 8603520 | 6/1986 | PCT Int'l Appl. . |
| 8604068 | 7/1986 | PCT Int'l Appl. . |
| 2171304 | 8/1986 | United Kingdom . |

OTHER PUBLICATIONS

Ramabhadran et al., PNAS U.S.A., vol. 81, pp. 6701–6705, Nov. 1984.
Sambrook et al., the EMBO Journal, vol. 4, pp. 91–103, Jan. 1985.
Ramabhadran et al., Gene, "High-Level Expression of the Bovine Growth Hormone Gene in Heterologous Mammalian Cells", 38:111–118 (1985).
Jacobs et al., Nature, "Isolation and Characterization of Genomic and cDNA Clones of Human Erythropoietin", 313:806–810 (2/85).
Miyake et al., J. of Biol. Chem., "Purification of Human Erythropoietin", 252:5558–5564 (8/77).

Primary Examiner—Alvin E. Tanenholtz
Attorney, Agent, or Firm—Mark A. Hofer; Paul T. Clark

[57] ABSTRACT

A rodent epithelioid cell transformed with a recombinant DNA vector including a DNA sequence encoding human erythropoietin, the transformed cell being capable of producing N-linked and O-linked glycosylated human erythropoietin.

10 Claims, 9 Drawing Sheets

```
-27                     -23                           -20                                        -10                  60
ATG GGG GTG CAC GAA TGT CCT GCC TGG CTG TGG CTT CTC CTG TCC CTG CTG TCG TCC CTC CCT
Met Gly Val His Glu Cys Pro Ala Trp Leu Trp Leu Leu Leu Ser Leu Leu Ser Leu Pro

+1                               +10                        120
CTG GGC CTC CCA GTC CTG GGC GTG GCC CCA GGC GCC CCA GTC CTG GGC ATC TGT GAC AGC CGA GTC CTG GAG
Leu Gly Leu Pro Val Leu Gly Val Ala Pro Gly Ala Pro Val Leu Gly Ile Cys Asp Ser Arg Val Leu Glu
                                                                                EPO1
                                                                +26 +27        +30                                   180
AGG TAC CTC TTG GAG GCC AAG GAG GCC GAG AAT ATC ACG ACG GGC TGT GCT GAA CAC TGC
Arg Tyr Leu Leu Glu Ala Lys Glu Ala Glu Asn Ile Thr Thr Gly Cys Ala Glu His Cys

+43                                          +50                                               240
AGC TTG AAT GAG AAT ATC ACT GTC CCA GAC ACC AAA GTT AAT TTC TAT GCC TGG AAG AGG
Ser Leu Asn Glu Asn Ile Thr Val Pro Asp Thr Lys Val Asn Phe Tyr Ala Trp Lys Arg

+55 +56               +60                                          +70                                       300
ATG GAG GTC GGG CAG CAG GCC GTC GRA GAA GTC CTG CAG GGC CTG GCC CTG CTG TCG GAA GCT
Met Glu Val Gly Gln Gln Ala Val Glu Val Leu Gln Gly Leu Ala Leu Leu Ser Glu Ala

+80                                          +90                                               360
GTC CTG CGG GGC CAG GCC CTG TTG GTC AAC TCT TCC CAG CCG TGG GAG CCC CTG CAG CTG
Val Leu Arg Gly Gln Ala Leu Leu Val Asn Ser Ser Gln Pro Trp Glu Pro Leu Gln Leu

+100                                         +110                                               420
CAT GTG GAT AAA GCC GTC AGT GGC CTT CGC AGC CTC ACC ACT CTG CTT CGG GCT CTG GGA
His Val Asp Lys Ala Val Ser Gly Leu Arg Ser Leu Thr Thr Leu Leu Arg Ala Leu Gly
                                                                                EPO2
        +115 +116                +120                                        +130                                    480
GCC CAG AAG GAA GCC ATC TCC CCT CCA GAT GCG GCC TCA GCT GCT CCA CTC CGA ACA ATC
Ala Gln Lys Glu Ala Ile Ser Pro Pro Asp Ala Ala Ser Ala Ala Pro Leu Arg Thr Ile

+140                                         +150                                               540
ACT GCT GAC ACT TTC CGC AAA CTC TTC CGA GTC TAC TCC AAT TTC CTC CGG GGA AAG CTG
Thr Ala Asp Thr Phe Arg Lys Leu Phe Arg Val Tyr Ser Asn Phe Leu Arg Gly Lys Leu

+160          +166
AAG CTG TAC ACA GGG GAG GCC TGC AGG ACA GGG GAC AGA TGA
Lys Leu Tyr Thr Gly Glu Ala Cys Arg Thr Gly Asp Arg End
```

EPO 140B

```
                                                                               31                                              61
  T CTG CCA GAG GGG AAG CCT CTG TCA CAC CAG GAT TGA ACT TTG GCC GGA GAA GTG GAT GCT
    -22                                                                                                                        121
    GAA TGT CCT GCC TGG CTG TGC CTT CTC TGC CTC CTG TCC CTG CTG TCG CTC CCT CTG GGC CTC CCA
        Cys Pro Ala Trp Leu Cys Leu Leu Ser Leu Leu Ser Leu Pro Leu Gly Leu Pro
    +1                                                                                                                         181
                                                                                               Kpn1
    GTC CTG GGC GCC CCA CCA CGC CTC ATC TGT GAC AGC CGA GTC CTG GAG AGG TAC CTC TTG
    Val Leu Gly Ala Pro Pro Arg Leu Ile Cys Asp Ser Arg Val Leu Glu Arg Tyr Leu Leu
                                                                                                                               241
    GAG GCC AAG GAG GCC GAG AAT ATC ACG ACG GGC TGT GCT GAA CAC TGC AGC TTG AAT GAG
    Glu Ala Lys Glu Ala Glu Asn Ile Thr Thr Gly Cys Ala Glu His Cys Ser Leu Asn Glu
                                                                                                                               301
    AAT ATC ACT GTC CCA GAC ACC AAA GTT AAT TTC TAT GCC TGG AAG AGG ATG GAG GTC GGG
    Asn Ile Thr Val Pro Asp Thr Lys Val Asn Phe Tyr Ala Trp Lys Arg Met Glu Val Gly
                                                                                                                               361
    CAG CAG GCC GTA GAA GTC TGG CAG GGC CTG CTG TCG GAA GCT GTC CTG CGG GGC
    Gln Gln Ala Val Glu Val Trp Gln Gly Leu Ala Leu Leu Ser Glu Ala Val Leu Arg Gly
                                                                                                                               421
    CAG GCC CTG TTG GTC AAC TCT TCC CAG CCG TGG GAG CCC CTG CAG CTG CAT GTG GAT AAA
    Gln Ala Leu Leu Val Asn Ser Ser Gln Pro Trp Glu Pro Leu Gln Leu His Val Asp Lys
                                                                                                                               481
    GCC GTC AGT GGC CTT CGC AGC CTC ACC ACT CTG CTT CGG GCT CTG GGA GCC CAG AAG GAA
    Ala Val Ser Gly Leu Arg Ser Leu Thr Thr Leu Leu Arg Ala Leu Gly Ala Gln Lys Glu
                                                                                                                               541
    GCC ATC TCC CCT CCA GAT GCG GCC TCA GCT GCT CCA CTC CGA ACA ATC ACT GCT GAC ACT
    Ala Ile Ser Pro Pro Asp Ala Ala Ser Ala Ala Pro Leu Arg Thr Ile Thr Ala Asp Thr
                                                                                                                               601
    TTC CGC AAA CTC TTC CGA GTC TAC TCC AAT TTC CTC CGG GGA AAG CTG AAG CTG TAC ACA
    Phe Arg Lys Leu Phe Arg Val Tyr Ser Asn Phe Leu Arg Gly Lys Leu Lys Leu Tyr Thr
                           +166 631                                                                                            661
    GGG GAG GCC TGC AGG ACA GGG GAC AGA TGA CCA GGT GTG TCC ACC TGG GCA TAT CCA CCA
    Gly Glu Ala Cys Arg Thr Gly Asp Arg End
```

FIG. 4-1

```
                                                                    691                        721
CCT CCC TCA CCA ACA TTG CTT GTG CCA CAC CCT CCC CCG CCA CTC CTG AAC CCC GTC GAG
GGG

EPO 125
                           XbaI      -22                                              62
GA  CTC TCA GCC TGG CTA TCT GTT CTA GAA TGT CCT GCC TGG CTG TGG CTT CTC CTG TCC CTG
                                      Cys Pro Ala Trp Leu Trp Leu Leu Leu Ser Leu
                                 92    +1                                             122
CTG TCG CTC CCT CTG GGC CTC CCA GTC CTG GGC GCC CCA CCA CGC CTC ATC TGT GAC AGC
Leu Ser Leu Pro Leu Gly Leu Pro Val Leu Gly Ala Pro Arg Leu Ile Cys Asp Ser
         KpnI                   152                                                   182
CGA GTC CTG GAG AGG TAC CTC TTG GAG GCC AAG GAG GCC GAG AAT ATC ACG ACG GGC TGT
Arg Val Leu Glu Arg Tyr Leu Leu Glu Ala Lys Glu Ala Glu Asn Ile Thr Thr Gly Cys
                                212                                                   242
GCT GAA CAC TGC AGC TTG AAT GAG AAT ATC ACT GTC CCA GAC ACC AAA GTT AAT TTC TAT
Ala Glu His Cys Ser Leu Asn Glu Asn Ile Thr Val Pro Asp Thr Lys Val Asn Phe Tyr
                      +55        272                                                  302
GCC TGG AAG AGG ATG GAG GTG AGT TCC TTT TTT TTT TTT CCT TTC TTT TGG AGA ATC
Ala Trp Lys Arg Met Glu

TCA TTT GCG AGC CTG ATT TTG G
```

PREP E C ELUTION
8

FIG. 9

CELL ENCODING RECOMBINANT HUMAN ERYTHROPOIETIN

BACKGROUND OF THE INVENTION

This invention relates to the use of recombinant DNA techniques to produce human erythropoietin (EPO).

EPO is a protein, normally produced in the liver of the fetus and in the kidneys of adults, which plays a role in the regulation of the oxygen level of the blood by stimulating the proliferation and differentiation of red blood cell Precursor cells to mature red blood cells. Purified EPO can be administered to human patients for the treatment of medical problems associated with inadequate red blood cell supply, e.g., anemia and chronic renal failure. EPO has been produced in cultured cells transformed with a vector containing a cDNA encoding EPO, e.g., as described in Kirin-Amgen PCT Application No. WO85/02610.

SUMMARY OF THE INVENTION

We have discovered that rodent epithelioid cells such as mouse C127 cells, when transformed with a recombinant DNA vector containing a DNA sequence encoding EPO, are capable of producing EPO of high biological activity which, like naturally-occurring EPO, is modified post-translationally by the addition of both N- and O-linked carbohydrates, which have attached a substantial amount of sialic acid, which is important in in vivo half-life. Presumably these post-translational modifications are enabled by the presence in the cells of the requisite enzymatic machinery.

We have found that the EPO produced by the recombinant cells of the invention have a different carbohydrate composition from urinary EPO, yet the recombinant EPO (rEPO) of the invention exhibits high biological activity.

Preferably, in the vector with which the cells are transformed, the EPO-encoding DNA sequence is under the transcriptional control of a eukaryotic metallothionein gene, and the vector further includes at least the 69% transforming region of the bovine papilloma virus genome (described in Howley et al., U.S. Pat. No. 4,419,446, hereby incorporated by reference).

The EPO of the invention exhibits good biological activity and is produced in high yield. In addition, the recombinant cells of the invention can be maintained in production in serum-free medium over a long period of time (at least 32 days). The use of serum-free media eliminates contamination of the final EPO product from non-EPO blood proteins, and greatly facilitates purification.

Accordingly, the invention also features a method of producing at least 99% pure EPO, involving (a) culturing recombinant EPO-containing rodent epithelioid cells in nutrient medium free of serum to produce EPO-containing medium, (b) clarifying the medium of cell debris to yield clarified EPO-containing medium, (c) subjecting the EPO-containing medium to ion exchange chromatography to yield partially purified EPO, (d) subjecting the partially purified EPO to reverse phase HPLC in an organic solvent to yield pure EPO in the organic solvent, and (e) removing the organic solvent.

In preferred embodiments of the method, step (e) is carried out by ion exchange chromatography or by solvent evaporation or solvent removal by dialysis, followed by gel filtration.

In other preferred embodiments, following step (b), the clarified EPO-containing medium is treated to inhibit proteolytic degradation of EPO during step (c), by removal of proteases in the clarified EPO-containing medium by fractionation on a dye column, or by the addition to the clarified EPO-containing medium of a protease inhibitor.

Other features and advantages of the invention will be apparent from the following description of the preferred embodiment thereof, and from the claims.

DESCRIPTION OF THE PREFERRED EMBODIMENT

The drawings are first described.

DRAWINGS

FIG. 1 is the nucleotide sequence of the coding region of human EPO (taken from Nature (1985), Vol. 313, p. 806) indicating the positions of two probes described herein ("EPO1" and "EPO2") which were used to isolate the gene; intron-exon junctions in the genomic clone are indicated by arrows.

FIG. 2 is a diagrammatic representation of the EPO gene in lamda EPO3, described herein.

FIG. 4 is a partial DNA sequence of EPO clones 104B and 125, described herein. Arrows denote intron-exon junctions. The XbaI and KpnI sites used in the construction of a full length EPO cDNA are shown.

Figure 2A:
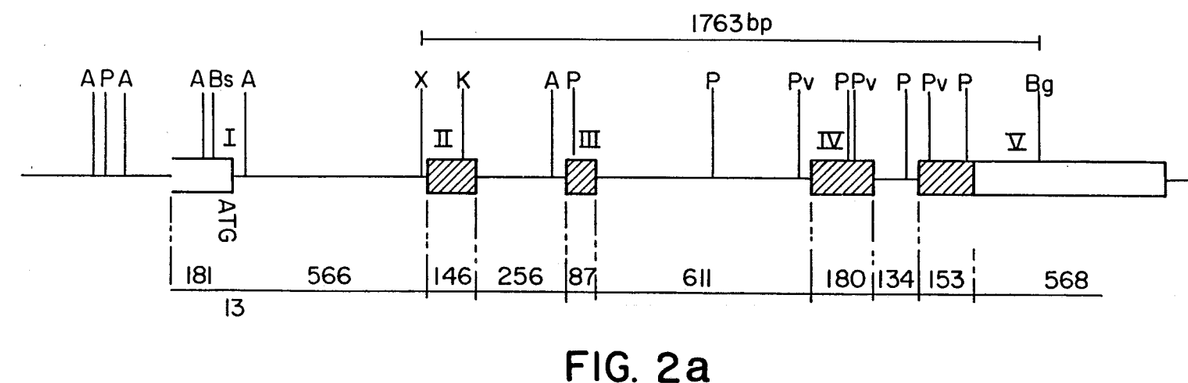
FIG. 2a gives confirmed restriction sites in lamda EPO3.
Figure 2B:
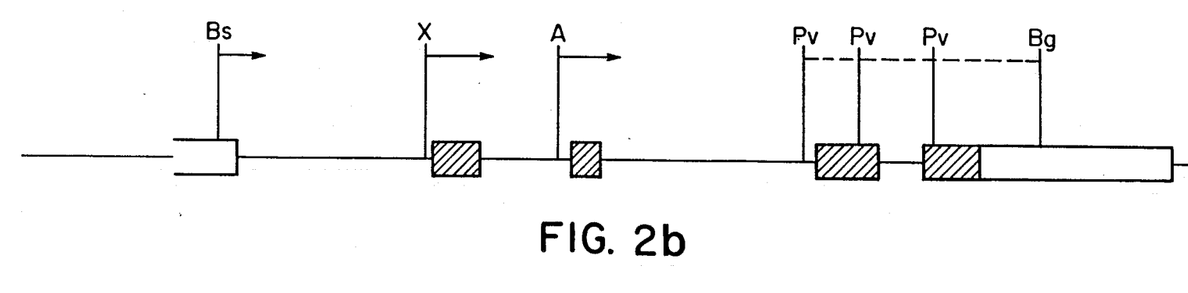
FIG. 2b illustrates the sequencing strategy for the EPO coding regions. Black boxes denote EPO coding regions; solid arrows denote regions sequenced by the Maxam-Gilbert method, and broken lines denote regions subcloned into pUC18 and sequenced by the Sanger method. Restriction sites are: A=AvaI; Bg=BglII; Bs=BstEII; K=KpnI; P=PstI; Pv=PvuII; X=XbaI.
Figure 5:
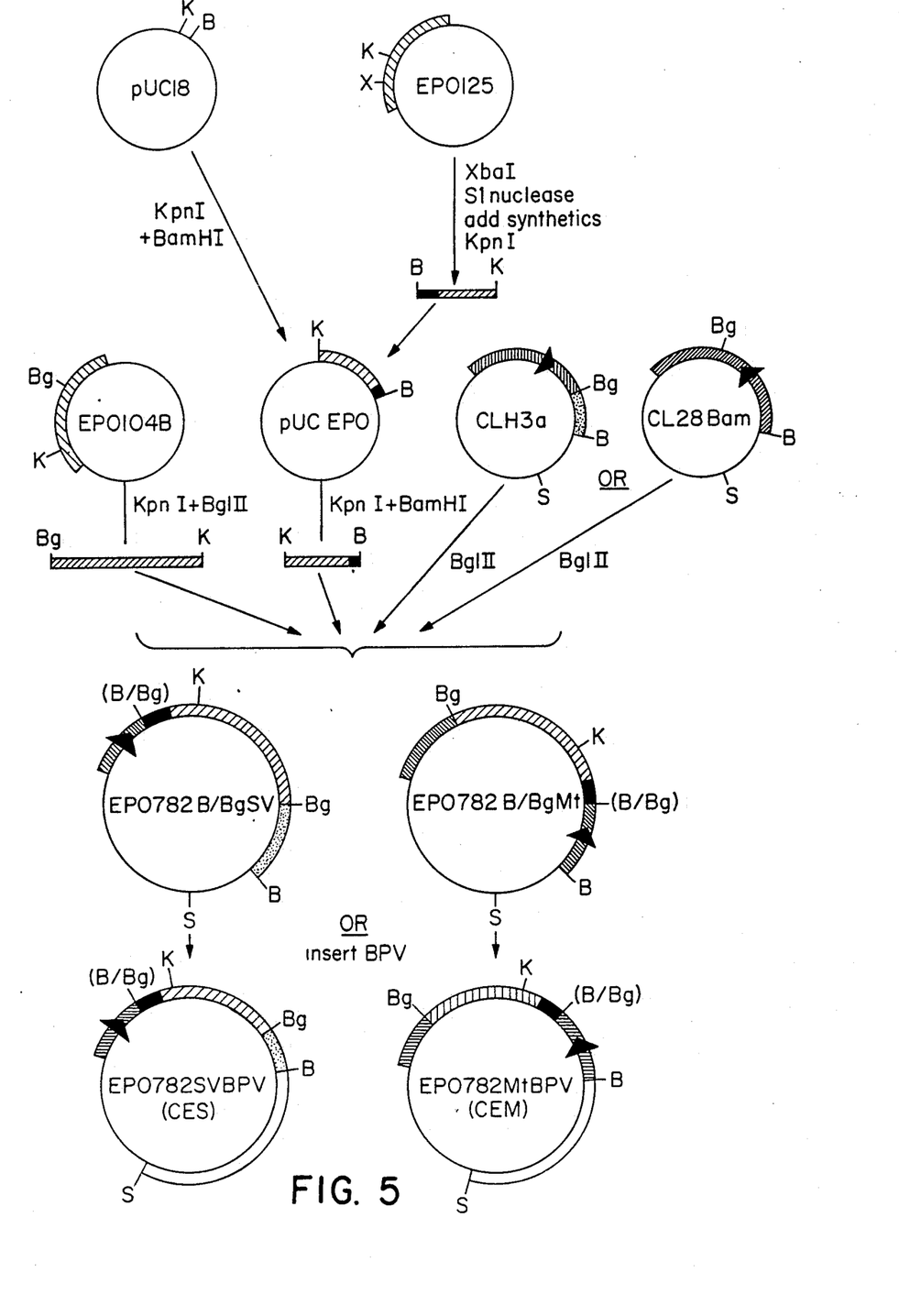
FIG. 5 is a diagrammatic representation of the construction of a full length EPO cDNA clone and its insertion into BPV-based expression vectors. Restriction sites are B=BamHI; Bg=BglII; K=KpnI; S=SalI; X=XbaI. The arrow denotes the MT promoter; filled-in boxes denote synthetic DNA; the botched box denotes EPO cDNA; double-hatched boxes denote MT non-promoter sequences; open boxes denote BPV sequences, lines indicate pBR322 sequences; and stippled boxes denote SV40 sequences.
Figure 6:
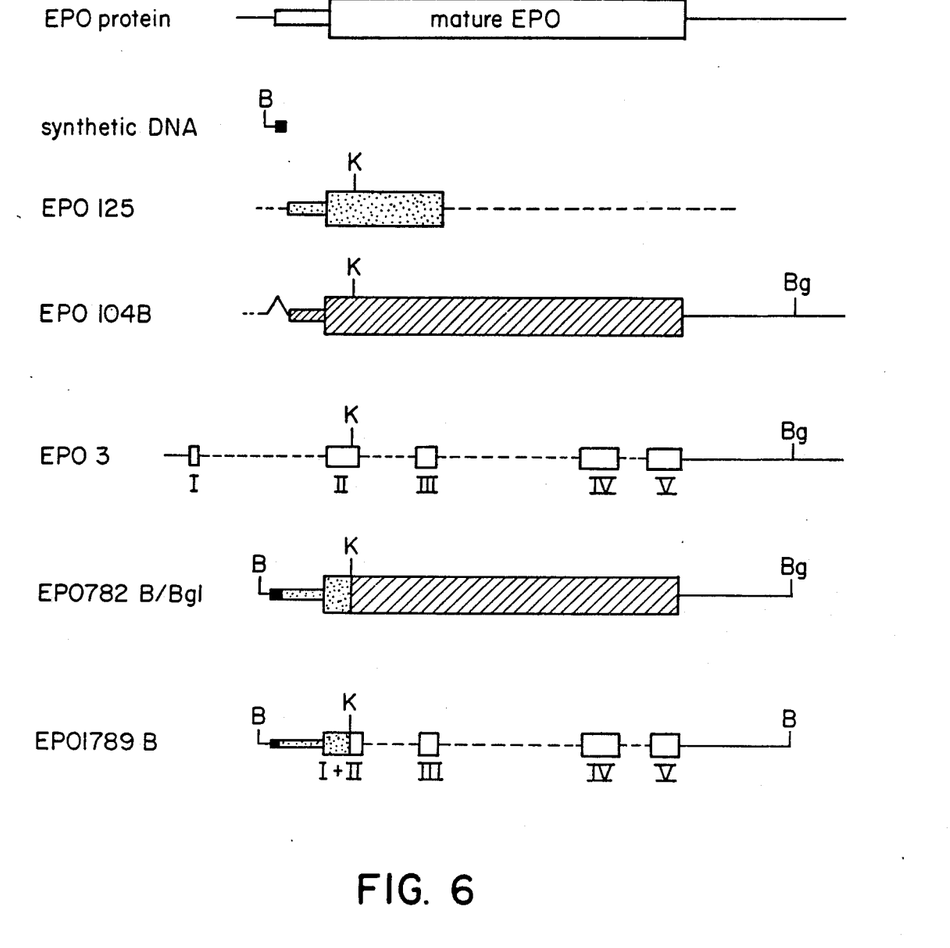
FIG. 6 is a diagrammatic representation of the construction of EPO782 B/Bgl and EPO1789 B. Coding regions are shown as boxes, intron sequences as broken lines. Restriction sites are: B=BamHI; Bg=BglII; K=KpnI.

ISOLATION OF THE HUMAN EPO GENE $5 \times 10^5$ plaques of a human genomic library (Lawn et al., 1978, Cell 15:1157) were screened by standard techniques with two synthetic DNA probes (EPO1 and EPO2, see FIG. 1) that correspond to portions of the published EPO DNA sequence (Jacobs et al., 1985, Nature, 313:806). One clone that hybridized to both probes (lambda EPO3) was analyzed by restriction mapping and shown to contain the entire EPO gene on a 20 kb EcoRI fragment (see FIG. 2). The exons of the EPO gene were sequenced and found to be identical to the published DNA sequence.

tion site available in this clone that could be used to attach the synthetic DNA coding for the first exon. In clone 125, on the other hand, there is an XbaI site just 5' of the second exon that could be used for a fusion of the synthetic DNA to the second exon. A full length cDNA could then be constructed by combining this exon 1-2 fusion in clone 125 with the 3' fragment of the cDNA of clone 104B at the common KpnI site. A detailed description of this construction is given below and is illustrated in FIGS. 5 and 6.

EPO125 was digested with XbaI, leaving a 4bp 5' overhang at the 5' end of exon 2. This single-stranded overhang was removed using exonuclease S1 to give blunt ends that start exactly at the second exon of EPO. To those ends, the following synthetic DNA fragments were ligated on:

|        | BamHI |   |   |   | EcoRI |   |   |   | −27 |   |   |   |   |   |   | −24 |   |   |
|--------|-------|---|---|---|-------|---|---|---|-----|---|---|---|---|---|---|-----|---|---|
| VV173: | 5' G  | A | T | C | C G   | A | A | T | T C | A | T | G | G | G | G | T G | C | A C G 3' |
| VV172: | 3'    |   |   |   | G C   | T | T | A | A G | T | A | C | C | C | C | A C | G | T G C 5' |

Isolation of human EPO cDNA clones

A cDNA library was constructed from mRNA isolated from a human fetus of about 20 weeks gestation by the insertion of dC-tailed cDNA into the dG-tailed plasmid vector pKT218 by standard cloning procedures. The library, consisting of about 140,000 clones, was screened with the synthetic DNA probes EPO1 and EPO2. Four positive clones were found.

Figure 3:
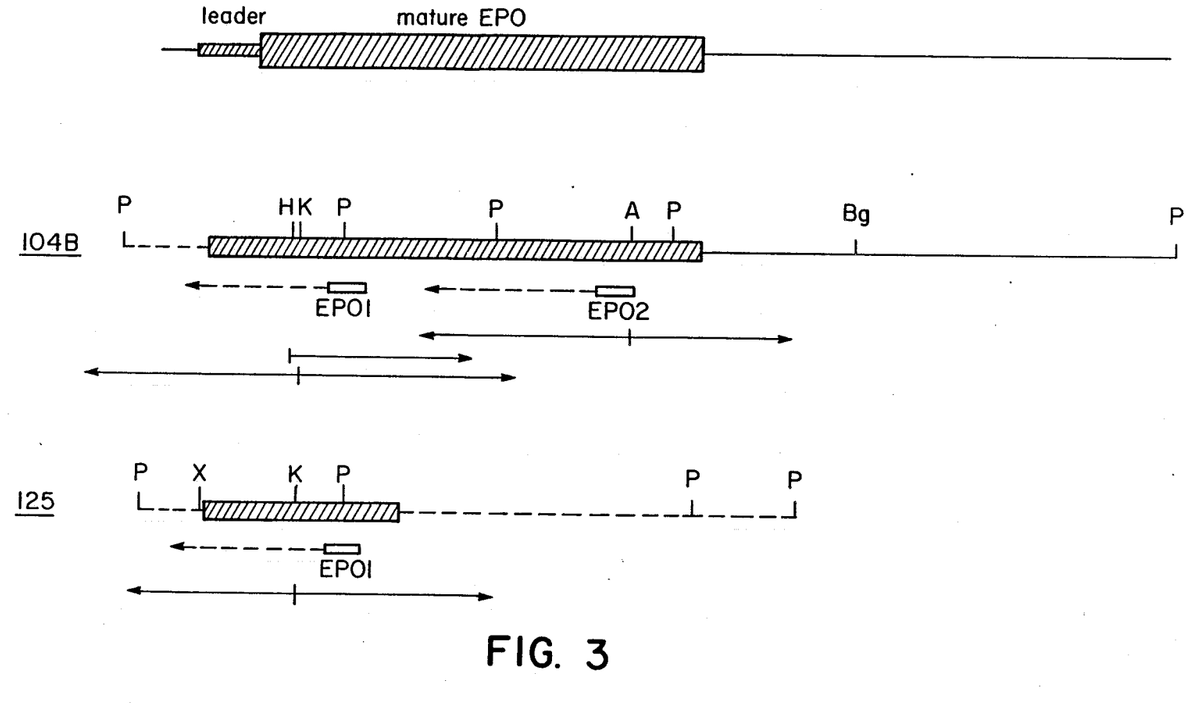
FIG. 3 is a set of diagrammatic illustrations of the EPO cDNA clones described herein, and the sequencing strategy employed. Broken arrows denote regions sequenced by the Sanger method, and solid arrows denote regions sequenced by the Maxam-Gilbert method. Restriction sites are: A=AccI; Bg=BglII; H=HinfI; K=KpnI; P=PstI; X=XbaI.

Clone 104B, which hybridized to probes EPO1 and EPO2 and clone 125 that hybridized to the 5' probe EPO1 only were analyzed further. Clones 104B (1330 bp long) and 125 (810 bp long) and the sequencing strategy are shown in FIG. 3. Partial DNA sequences of these clones are given in FIG. 4.

The sequence of clone 104B between nucleotides 63 and 724 has 100% homology with the published DNA sequence of the EPO cDNA. This clone thus contains the entire coding sequence for the 166 amino acids of the mature EPO protein and for 22 amino acids of the leader sequence. The first 13 nucleotides of the coding region are missing in this clone, and are replaced by 62 nucleotides that originate from the intron between exons 1 and 2 of the EPO gene. The RNA from which this sequence was derived probably resulted from an aberrant splicing event.

A comparison of the sequence of clone 125 with the published EPO sequence showed that this clone codes for amino acids −22 to +55 of the EPO protein. At the 5' end of this clone are 72 nucleotides of the intron between exons 1 and 2 (only 27 nucleotides are shown in FIG. 4) and at the 3' end are approximately 460 nucleotides of the intron between exons 3 and 4 (only the first 64 nucleotides of this intron were sequenced). The intron between exons 2 and 3 has been spliced out correctly.

Construction of a full length EPO cDNA clone and its insertion into mammalian expression vectors Since none of the cDNA clones contains the complete EPO coding region, the 13 nucleotides of the first exon of EPO that code for the amino terminus of the leader peptide were synthesized. Due to the aberrant splicing in clone 104B, there was no convenient restric- These linkers contain a BamHI overhang at the 5' end for insertion into BPV based expression vectors (see below) followed by an EcoRI site for insertion into SV40 vectors, as well as the 13 nucleotide coding region of the first exon of the EPO gene. In order to avoid self-ligation of these linkers at the BamHI overhangs, only VV172 was kinased. After addition of the linkers, EPO 125 was digested with KpnI, and the 137 bp BamHI-KpnI fragment was isolated and ligated into BamHI plus KpnI cut pUC18 to yield pUCEPO.

Four single clones of this construction were sequenced and found to have the expected sequence with the correct fusion of the synthetic DNA and the second exon at the modified XbaI site. The 137 bp BamHI-KpnI fragment of pUCEPO coding for the 5' portion of EPO and the 649 bp KpnI-BglII fragment of EPO 104B coding for the 3. portion of EPO were isolated and ligated into the alkaline phosphatase treated BglII site of vectors CL28Bam and CLH3a, respectively (see below). The 5' to 3' orientation of the EPO cDNA insert within the vectors was checked by restriction mapping. The resulting plasmids, EPO782 B/Bgl Mt and EPO782 B/Bgl SV were digested with BamHI and SalI and the BPV genome (publicly available; see Howley et al., id) was inserted as a BamHI-SalI fragment to yield the expression plasmids EP0782 Mt BPV and EPO782 SV BPV.

Construction of a modified EPO gene suitable for insertion into mammalian expression vectors Because of the high incidence of cDNA clones isolated that have incompletely removed the first intron of the EPO gene (see above and also Jacobs et al., id.), a modified EPO genomic clone was constructed from which the first intron had been removed by genetic engineering. This could be conveniently carried out by combining the 5' portion of the cDNA clone EPO782 B/Bgl with the 3' sequences of the EPO gene at the single KpnI site which is located in the second exon of the gene. This construction is described in detail below and illustrated in FIGS. 6 and 7.

Figure 7:
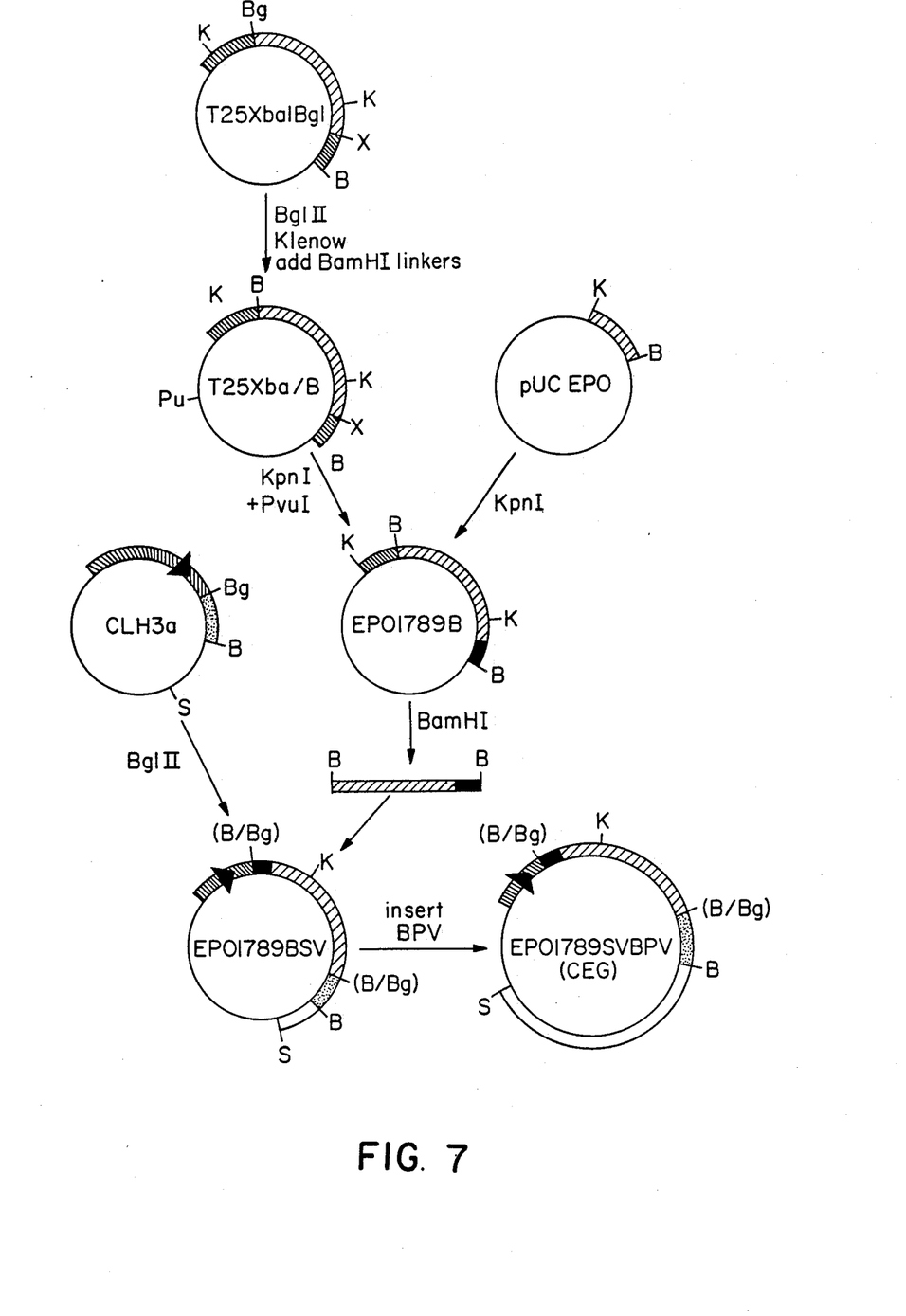
FIG. 7 is a diagrammatic representation of the construction of an EPO genomic coding sequence suitable for insertion into BPV-based expression vectors. Boxes and restriction sites are as in FIG. 5, and Pu=PvuI.

The 1763bp long XbaI-BglII fragment of lambda EPO3 (see FIG. 2), containing all but the first exon of EPO, was subcloned into T25B, a vector containing single XbaI and BglII sites to yield plasmids T25Xba/Bgl (see FIG. 7).

T25Xba/Bgl was digested with BglII, the overhangs were filled in using the Klenow fragment of DNA polymerase, BamHI linkers were added, and the vector was circularized. The 2.3 kb KpnI fragment of T25Xba/B containing the 3' portion of the EPO gene and some metallothionein sequences was then ligated into KpnI-cut pUC EPO (see FIG. 5) to give EPO1789B. This plasmid contains the desired EPO gene from which the first intron has been removed. The EPO-containing BamHI fragment from EPO1789B was isolated and ligated into the BglII site of CLH3a to yield Plasmid EPO1789BPV. The 5' to 3 orientation of the EPO clone within the vector was checked by restriction analysis. Into this plasmid was inserted the BPV genome as a BamHI-SalI fragment to yield expression plasmid EPO1789SVBPV.

Expression Vectors and transfection of Mammalian Epithelioid Cells

The EPO cDNA and the modified genomic clone can be inserted into any suitable mammalian expression vector, most preferably those that can be used to transform rodent epithelioid cells such as mouse C127 cells. Preferred expression vectors are the BPV vectors described in Wei et al., U.S. Ser. No. 782,686, filed October 1, 1985, assigned to the same assignee as the present invention and hereby incorporated by reference, and Hsiung et al., 1984, J. Molec. and App. Genet, 2:497. The vectors (FIGS. 5 and 7) include a mouse metallothionein promoter (MT) from which inserted genes can be transcribed, and bovine papilloma virus DNA (BPV) to effect transfection of mammalian cells. The vector CLH3a also includes late promoter poly-adenylation sequences derived from SV40 virus, which can affect expression from a gene inserted into the vector. The illustrated expression plasmids also include a portion of the E. coli plasmid pML, which permits shuttling between prokaryotic and eukaryotic systems. No selection is required for the maintenance of these plasmids in host cells, and they are maintained in high copy number (approximately 50–100 copies/cell). The EPO cDNA and the modified EPO genomic clone were inserted into these BPV vectors as described above. The final expression vector constructs are shown in FIGS. 5 and 7. As a matter of convenience, the names of the expression vectors have been shortened to CEM, CES and CEG for EPO782MtBPV, EPO782SVBPV, and EPO1789SVBPV, respectively. These vectors were transformed into E. coli strain MC1061 using conventional methods and grown in bulk culture. The DNAs were purified by CsCl banding before transfection into mammalian cells.

On separate days, three to five sets of transfections with the different vectors into mouse C127 cells (commercially available) were carried out as follows:

Mouse C127 cells were maintained in Dulbecco's modified Eagle's medium (DME) supplemented with 10% fetal calf serum and 10mM glutamine as described in Hsiung et al., id. DNA transfections were carried out by the method described in Wilger et al. 1977, Cell 11:233, as modified by Hsiung et al., id. Ten to twenty micrograms of calcium phosphate precipitated DNA was incubated for six to eight hours at 37° C. with $1 \times 10^6$ cells in fresh culture medium. The medium was removed and the cells treated with 20% glycerol in 10 mM phosphate-buffered saline (PBS), pH7.0, for one to two minutes at room temperature, washed twice with PBS and fresh DME added. The cells were then incubated at 37° C. and the medium replaced after 24 hours and every three to four days thereafter.

EPO expression

Foci, representing BPV transformed C127 cells, were detectable 10–14 days after transfection. Supernatants from Plates containing transformants were assayed 17 days after transfection by the $^3$H-thy uptake assay (Krystal 1983, Exp. Hematol., 11/7, 649) and found to contain EPO. 2½ to 3 weeks after transfection, foci were isolated by the cloning ring method and transferred to T-25 flasks. After the cells reached approximately 20% confluency, the supernatants were tested for EPO production by the $^3$H-thy uptake assay. A total of 76 cell lines (15 CEM, 35 CES and 26 CEG transformants) were transferred into T-75 flasks.

When the cells were confluent, the supernatants were assayed for EPO expression and the cells were counted and frozen. To test the reproducibility and stability of these cell lines, the 21 highest producing cell lines were thawed and rescreened for 24 hours expression levels on a per cell basis. The five highest producers (3CES and 2CEG transformants) were chosen and expanded into roller bottles to test for growth and production properties. Representative 24 hour culture fluids from cell lines CES9dog and CEG4d in T-75 flasks contained 600U/ml and 800U/ml of rEPO as measured by the $^3$H-thy uptake assay using human urinary EPO as a standard and 490 and 540U/ml when measured by the $^{59}$Fe incorporation assay into rat bone marrow cells in vitro (Goldwasser et al., 1975, Endocrinology 97:315.). These samples were also active in vivo in the Polycythemic mouse assay as described by Cotes et al., 1961, Nature 191:1065.

Production of Recombinant Human EPO

Production of EPO from transformed C127 cells in serum-free medium was achieved by expanding the cells in serum containing medium in roller bottles, transferring the cells onto microcarrier beads in spinner culture vessels, and replacing the serum-containing growth medium with serum-free production medium once the cells had reached saturation density. The conditioned culture medium was then regularly replaced with fresh serum-free medium and the vessels kept in a continuous production for months without the addition of any serum. This method allows economical production of large quantities of serum-free conditioned medium from which recombinant human EPO can readily be purified (see below).

Cells from cell line CES9dog are grown in roller bottles containing DME+10% FBS under standard culture conditions. The procedure for the preparation and inoculation of microcarrier spinner cultures is similar for all vessel sizes ranging from 100 ml to 15L. All microcarrier spinners are provided by the Bellco Glass Company. Before each use, the individual spinners are freshly washed, air dried and then have a thin coating of silicone (Sigmacote, Sigma Chemical Co.) applied to the interior glass surface. After drying, the vessels are extensively rinsed with distilled water before use.

The microcarrier beads of choice for production of EPO are Cytodex 3 (Pharmacia). Final microcarrier concentration in all suspension vessels is 5 gm/liter of culture media. The vessel is filled with one-half of its final working volume with PBS and the appropriate amount of dry microcarrier beads are added. The beads are allowed to swell for three hours at room temperature. They are then rinsed twice with PBS by decanting and the vessel volume returned to one-half of its working volume. The vessel is loosely capped, prepared for autoclaving and then steam sterilized for one hour at 121° C. (two hours for the 15L vessels). After cooling to room temperature the PBS is withdrawn to 20% of final working volume and DMEM is added to the final volume. The culture is then stirred for 30 minutes at 37° C. After stirring, the beads are allowed to settle and 80% of the supernatant is replaced with fresh growth media with 10% FBS. The vessels are now ready for inoculation.

As an example, two 15 liter spinner flasks were seeded with cells from the CES9dog line. Each spinner was seeded with freshly trypsinized cells from 15 roller bottles in 10 liters of growth medium (DMEM+10% FBS) and 5 g/liter of Cytodex 3 beads. The initial concentration of cells in the vessels was $1 \times 10^5$ cells/ml. The cultures were then placed on magnetic stirrers (Bellco) and grown at 37° C. The 10 liter spinners were stirred at 20 rpm. The cultures were sampled daily and on day two, 80% of the growth medium was replaced with fresh medium. At this point, the overlayer aeration was started by flushing the head space with a mixture of 95% air/5% $CO_2$. On day four, the growth medium was replaced again. On day six the cell numbers were between 1.75 to $2.5 \times 10^6$ cells/ml. Cells were enumerated by counting nuclei (Levine et al., Somatic Cell Genetics (1977) 3:149).

At this point, the spinner cultures were transferred to the production phase: the growth medium was exchanged twice (80% volume exchange each time) with DMEM without serum and after the second rinse, the medium was replaced with CEM2000 without serum (Scott Labs). The cultures were sampled every day for EPO production. Every 48 hours 80% of the conditioned medium was collected and replaced with an equal volume of fresh CEM2000 (eight liters per spinner). The medium from both vessels were pooled on each collection day and submitted for purification. Representative serum-free media harvested from 10L spinner cultures (described above) contained human EPO at a concentration of approximately 600 U/ml as judged by the $^3$H-thy incorporation assay and an EPO radioimmunoassay using human urinary EPO as a standard.

As another example, six one liter spinner flasks were seeded with CES9dog cells in DMEM+10% FBS. After the cells had reached saturation density, the vessels were put into production by replacement of 80% of the growth medium with serum-free production medium as described above. The media from duplicate vessels were harvested every 48, 72 or 96 hours, respectively. The average EPO production in these one liter spinners was 576, 698 and 842 units per 24 hours as measured by RIA for the 48, 72 and 96 hour harvest schedules, respectively. At 32 days, the cells were still producing EPO at the same levels.

Purification of Recombinant EPO

Recombinant human EPO can readily be purified from serum-free medium conditioned by mammalian cells producing rEPO. The purification to homogeneity generally involves the steps of: (1) clarification, concentration and dialysis of culture medium; (2) ion-exchange chromatography; (3) reverse phase high performance liquid chromatography (RP-HPLC); and (4) gel filtration or ion exchange chromatography. Steps 1 and 2 will remove from the culture medium proteases and some serum components remaining in the production medium (specifically in harvests shortly after switching the cultures from serum containing growth into serum-free production medium); steps 2 and 3 give a major purification, and step 4 is designed to remove the organic solvent used in step 3 and to elute the purified EPO in the final formulation buffer. These steps are described in more detail below. All purification procedures are carried out at 4° C. with the exception of the RP-HPLC step, which is carried out at room temperature.

As an example, pure, homogeneous rEPO was prepared from 11.75 liters of serum-free EPO production medium harvested from the 10 liter spinner cultures described above. EPO levels were measured throughout the purification process using the $^3$H-thy incorporation assay and an EPO RIA. All dose response curves at the different purification stages were parallel to each other and to the human urinary standard.

(1) Clarification, concentration and dialysis of culture medium 11.75 liters of CES9dog conditioned serum-free media, harvested from 10 liter spinner flasks and containing approximately 700 units of EPO per ml, were made 0.01% in Tween 80, and then clarified of cell debris and microcarriers by passage through a 0.5 um Pall Profile ™ filter cartridge at a flow rate of 2.5 L/minute. The pressure of the cartridge did not exceed 20 psi. The clarified media were then concentrated 10-fold and flow dialyzed into 50 mM Na Acetate, pH5.0 containing 15 mM NaCl, and 0.01% Tween 80 to a final conductivity of 6.90 mS/cm$^2$. This was accomplished with a tangential flow system: an Amicon Spiral Ultrafiltration S10Y10 cartridge having a YM 10,000 MW cutoff membrane was used at a retention flow rate of 1.5–2 L/minute, a breakthrough flow rate of 0.4–0.8 L/minute, and a back pressure maintained at 25–30 psi. The volume of the final concentrate was 970 ml, its pH was 5.0, and its conductivity 6.90 mS/cm$^2$. EPO recovery through these steps is greater than 90%.

(2) Ion exchange chromatography

A screen of ion exchange resins demonstrated that relatively high ionic strength resins are best suited for the purification of EPO. In this particular example, an S-Sepharose Fast Flow column from Pharmacia was used. A 2.5 cm×12.5 cm (60 ml) column was equilibrated at 4° C. with 50 mM Na Acetate, pH 5.0, containing 15 mM NaCl, and having a conductivity of 6.90 mS/cm$^2$. The absorbence of the column effluent was monitored at 280 nm with an in-line detector (LKB). The column was loaded with 960 ml of the concentrated media at a flow rate of 5 ml/minute (61.6 cm/hour) and the column was washed with equilibration buffer until the absorbence returned to baseline (approximately 2 column volumes). The column was eluted with a 300 ml linear salt gradient of 0.015 M to 0.4 M NaCl in 50 mM Na Acetate, pH5.0. Fractions (6 ml) were collected into tubes containing 0.15 ml of 2M Tris-HCl, pH8.8. This adjusted the pH of the effluent to approximately 8.0 and gave a final Tris concentration of 0.05 M. Finally, the column was washed with 0.05 M Tris-HCl, pH9.0, containing 2 M NaCl. EPO-containing fractions were pooled.

The S-Sepharose Fast Flow column gave an approximately 7-fold purification and a recovery of about 60%. Losses at this step are due to proteases present in the conditioned medium which are active at pH5.0 (which is the optimal pH for EPO purification with this resin).

(As is described below, losses at this step can be minimized by the use of immobilized dyes or protease inhibitors.)

(3) Preparative Reverse Phase HPLC

HPLC was carried out with a Waters high pressure liquid chromatography system consisting of a model 6000A solvent delivery system and a model 660 solvent programmer. A 2.2 cm×25 cm preparative $C_8$ column (Amicon 10 um particle size, 100 A pore size) was equilibrated at room temperature with 10 mM $NaPO_4$, pH6.0 buffer. (A column of different carbon length, e.g., $C_4$–$C_{18}$, can also be used, but are less preferred.). The pooled S-Sepharose sample was prefiltered through a 0.45 um Gelman Acrodisk filter and loaded onto the column by repeated injections using a 2 ml sample loop. The column was run at 6 ml/minute (71.0 cm/h) and the absorbence of the effluent was monitored at 280 nm. Following loading the sample, the column was washed with 10 mM $NaPO_4$, pH6.0, until the absorbence returned to baseline. The column was eluted with a 2.5h linear 0% to 40% n-propanol gradient (in 10 mM $NaPO_4$, pH6). One minute fractions (6 ml) were collected.

Figure 8A:
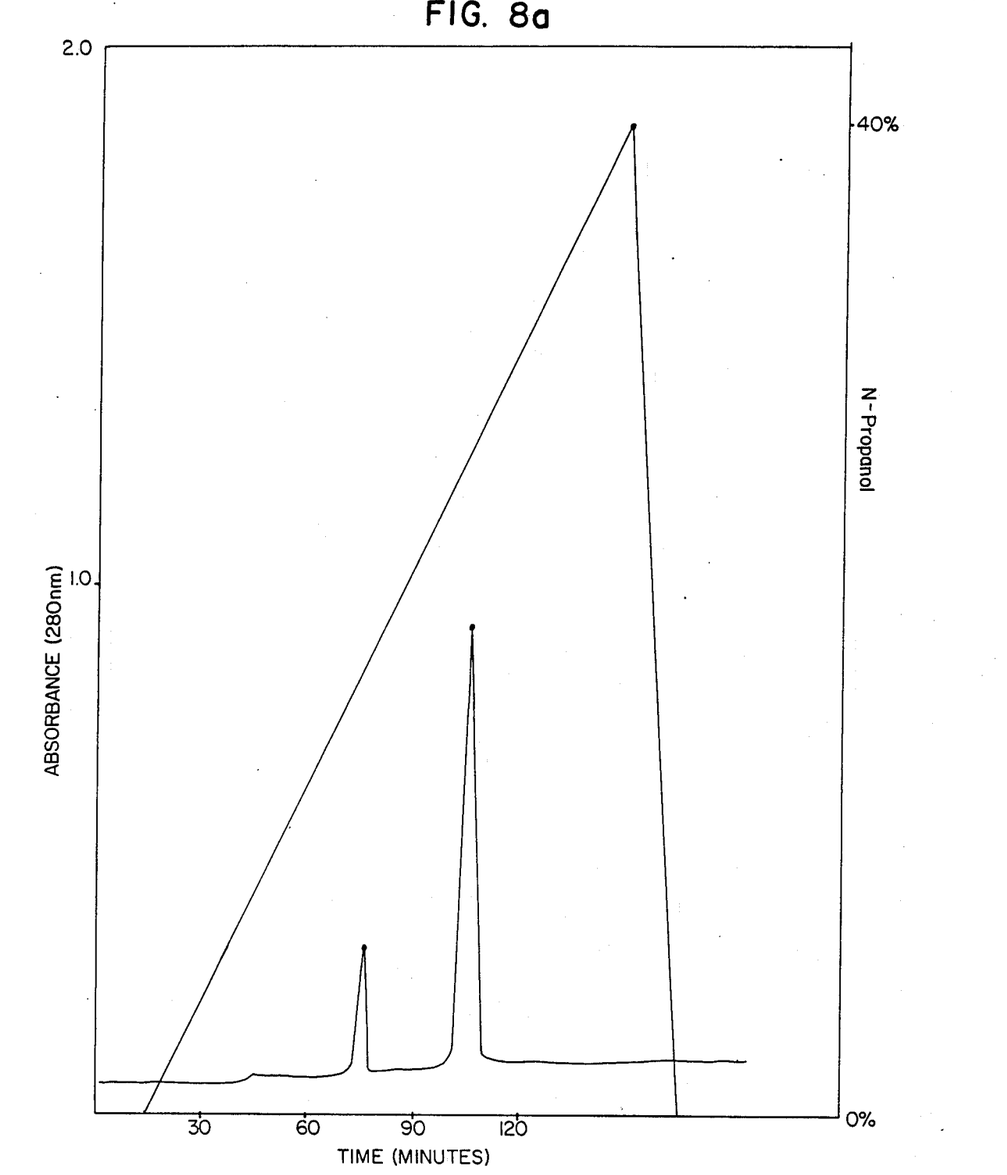
FIG. 8a is an absorbance (280 nm) profile of the n-propanol elution of EPO from a reverse phase $C_8$ column; the elution gradient was 0–40% n-propanol in 10 Mm phosphate, pH 6.0.
Figure 8B:
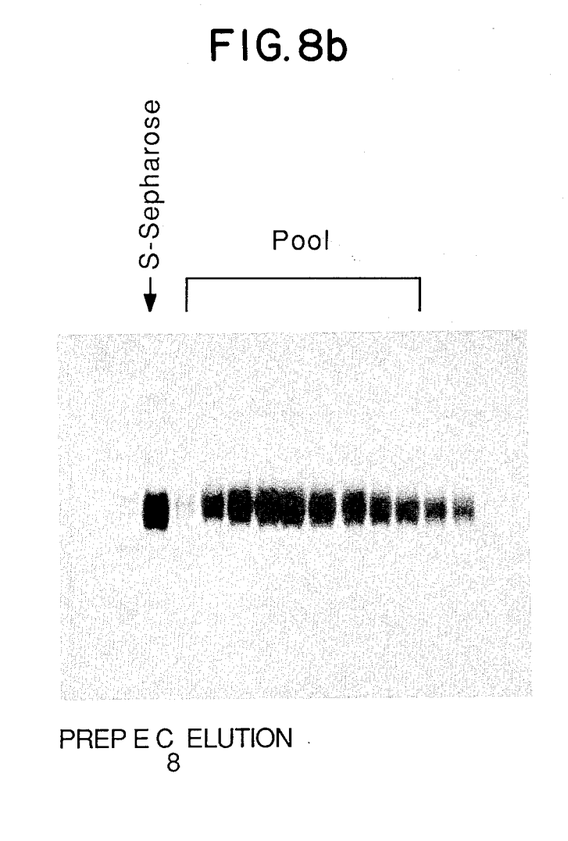
FIG. 8b shows SDS PAGE of fractions from the $C_8$ column; the fractions were analyzed with a 10% gel and stained with coomassie; fractions were pooled as indicated.

Several small peaks of material absorbing at 280 nm were eluted between 60 minutes and 95 minutes of the gradient and a single, sharp peak eluted between 100 minutes to 110 minutes (FIG. 8). The elution peaks were analyzed by SDS PAGE. The EPO containing fractions coincided with the large peak at 100 minutes to 107 minutes (approximately 25% Propanol). A laser densitometer scan of the coomassie stained SDS gel indicated that the EPO was greater than 99% pure at this stage. In this example, the $C_8$ step gave a 2-fold purification.

The recovery of immunological and of in vitro biological activity at this step was high (83%), indicating that n-propanol had no adverse effects on the in vitro biological activity.

(4) Gel Filtration Chromatography

To ensure complete removal of the organic solvent and to elute the purified EPO in a desired physiologically compatible buffer, the $C_8$-purified material can be further fractionated by gel filtration chromatography. If the gel filtration resin is not compatible with high concentrations of organic solvents, a flow-dialysis step must be used prior to gel filtration in order to remove the majority of the organic solvent. If the resin matrix of the last column is resistant to the organic solvent used, the pooled fractions from the RP-HPLC step can be passed directly over this column under conditions where the protein binds to the resin and the organic solvent flows through. The organic solvent can then be washed out extensively with an aqueous buffer and the protein can finally be eluted from the column.

The elution pool from the $C_8$ column was made 1% mannitol and 0.5M NaCl by the addition of solid material, and then introduced into an Amicon stir cell having a YM10 (10,000 M.W. cutoff) ultrafiltration membrane. The volume was reduced approximately ten fold and then restored to the original volume with 15mM $NaPO_4$, pH7.2, containing 0.5M NaCl and 1% mannitol. The process was repeated twice and the dialyzed pool was concentrated to a final volume of 17.5ml. Analysis of this process for total protein using the Lowry method showed greater than 98% recovery. Fourteen ml of the dialyzed material was then fractionated by gel filtration chromatography.

A 2.5cm×98 cm (481 ml) column of GC200 Cellufine filtration resin (Amicon) was equilibrated at 4° C. with 15 mM $NaPO_4$, pH7.2 buffer containing 0.5M NaCl and 1% mannitol at a flow rate of 0.8 ml/minute (9.8cm/hour). The 14 ml sample was loaded, the column effluent was monitored at 280 nm, and 6 ml fractions were collected. A single, symmetrical peak was eluted and SDS PAGE confirmed the peak to be EPO. No further purification of EPO was achieved at this step and the recovery was 89%.

EPO produced by the above purification method was shown to be greater than 99% pure as judged by SDS-PAGE and to have high potency in in vitro and in vivo biological assays. The overall EPO yield in this example was 41%.

The addition of a dye column to step 1 gives some additional purification and, more importantly, removes contaminating proteases from EPO and consequently allows higher EPO recoveries at the S-Sepharose Fast Flow step. The clarified media was loaded on a Blue Trisacryl-M column (Pharmacia) equilibrated with 10 mM $NaPO_4$ pH6.0, 150 mM NaCl and eluted with a linear salt gradient of 0.15 to 2.5 M NaCl in 10 mM $NaPO_4$ pH6.0 and then flow-dialyzed into 50 mM Na Acetate, pH5.0 containing 15mM NaCl. The recovery of EPO from the Blue Trisacryl column was almost complete and the recovery on the following S-Sepharose Fast Flow column was 86% compared to 60% in example 1. EPO containing 10X concentrated medium or partially purified step 2 material has been shown to degrade rapidly (t½ approx. 4h) when incubated at 37° C. under mildly acidic conditions at pH5.0. This degradation seems to be caused by proteases that are active at PH5.0. The improved yields in step 2 as illustrated in this example can be attributed to the separation of proteases from the EPO protein by the Blue Trisacryl column. (Other commercially available dyes can also be used.)

Figure 9:
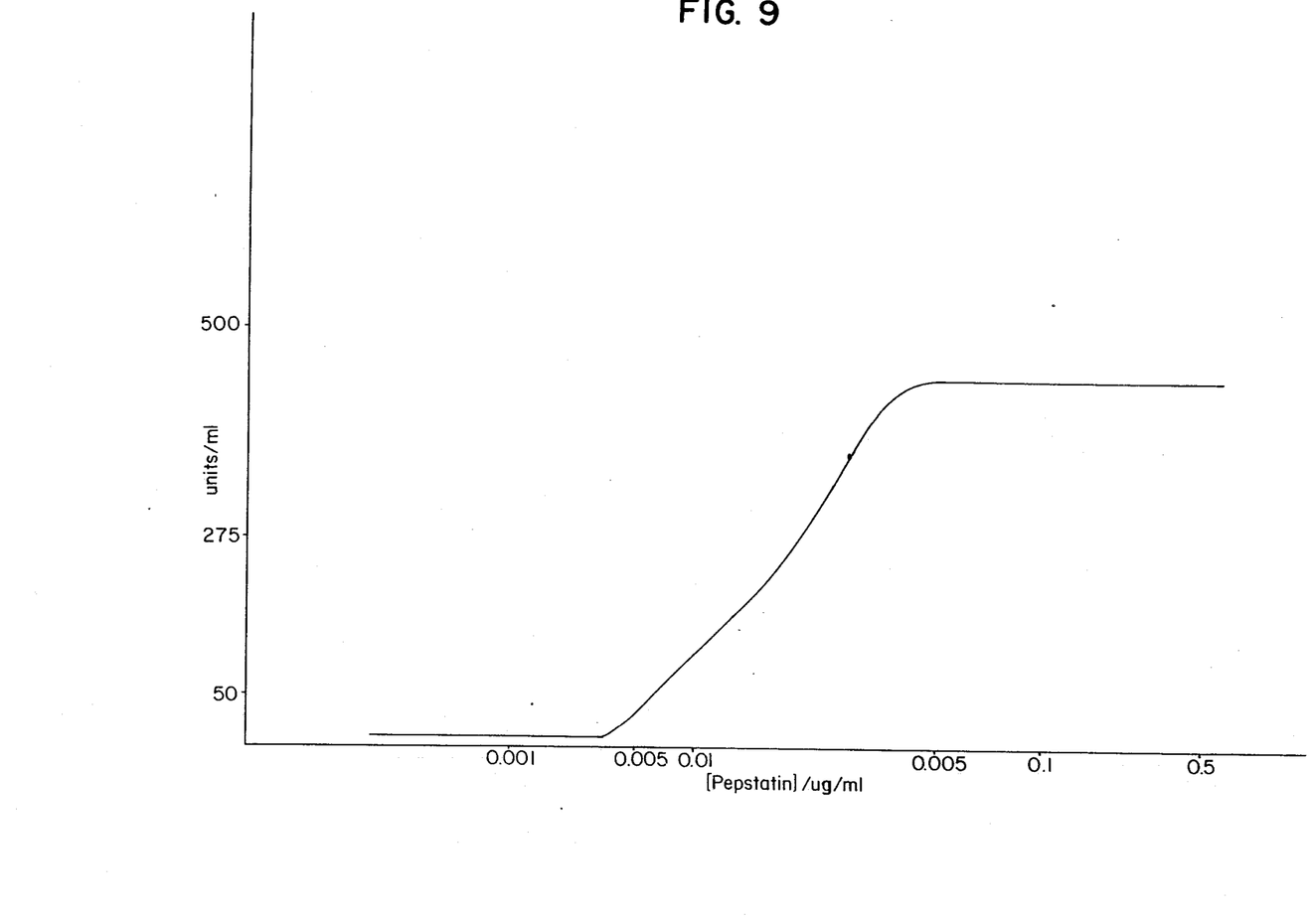
FIG. 9 is a graphical illustration of the stabilization of EPO at pH 5.0 by the protease inhibitor pepstatin.

Protease inhibitors can also be added to the conditioned medium in order to improve EPO yields. Several commercially available protease inhibitors were tested to see if they could prevent EPO degradation at pH5.0. 10X concentrated (Step 1) EPO medium was diluted 1:10 in 50mM Na Acetate, pH5.0 and then incubated at 37° C. with or without protease inhibitors at a concentration of 5 micrograms/ml. Aliquots were taken over a period of 29 hours and assayed by RIA. This experiment showed that pepstatin (Sigma) had a significant stabilizing effect on EPO immunoactivity over this time period at pH5.0. Pepstatin was then tested to determine the minimum concentration at which it is effective. Under the same conditions as described above, pepstatin was included into 10X concentrated medium over range of 0.0005 to 1ug/ml and incubated at 37° C. for 25 hours. The $IC_{50}$ (the concentration at which 50% of the proteases are inhibited) of Pepstatin is approximately 0.02ug/ml (FIG. 9). To test the effect of pepstatin in the purification process, 0.2ug/ml of pepstatin was added to the 10X concentrated medium and to the buffers for the S-Sepharose column. Under these conditions, 97% of EPO was recovered from the S-Sepharose Fast Flow column compared to approximately 60% without the use of a protease inhibitor.

The gel filtration chromatography step (Step 4, above) can be replaced by an S Sepharose Fast Flow ion exchange step to remove organic solvents. Fractions containing EPO eluted from the $C_8$ column at approximately 25% propanol were pooled, the pH was lowered to 5.0 by dilution with nine volumes of 0.05M Na Acetate buffer, pH5.0 and then applied to a S-Sepharose Fast Flow column equilibrated in 50 mM Na Acetate pH5.0 containing 15 mM NaCl. The column was washed with several volumes of this buffer and EPO was then eluted with PBS pH8.0. EPO recovery at this step was quantitative and the final product was found to be free of residual propanol.

Characterization of the purified rEPO rEPO purified from medium conditioned by CES9-dog cells as described above was partially characterized and compared to human urinary EPO. Analysis of the rEPO by SDS-PAGE followed by coomassie blue and silver staining showed that rEPO purified by this method was greater than 99% pure. It migrates with an apparent molecular weight of approximately 34K on SDS-PAGE as a single protein band.

The amino acid sequence of purified rEPO was determined by both N-terminal sequencing and enzymatic digestion of the rEPO, separation of the created peptides by reverse phase HPLC and sequencing of these peptides using a gas phase sequencer. More than 95% of the EPO molecule has been sequenced. The following observations have been made: the amino acid sequence of rEPO produced by BPV transformed C127 cells is indistinguishable from that of human urinary EPO. In particular, the amino-terminal sequence analysis indicated that the hydrophobic leader peptide is cleaved at the correct position. No signal for any PTH (Phenyl-thiohydantoins) amino acid was observed at positions 24, 38 and 83 of the EPO peptide. These positions correspond to Asn in the EPO sequence, which represent possible sites for the addition of N-linked carbohydrates (Asn-X-Ser or Thr, Neuberger et al., 1972: The Glycoproteins: Their Composition, Structure and Function, p. 450). This data and the results of carbohydrate analysis of EPO strongly suggests that in rEPO produced in C127 cells all three possible N-glycosylation sites are indeed glycosylated. Amino acid position 126 corresponds to a serine in the nucleic acid sequence. No signal for any PTH amino acid was seen at this position. Carbohydrate analysis of a peptide containing this residue indicated the presence of galactose, indicating that Ser126 is O-link glycosylated. Carbohydrate analysis of rEPO revealed the presence of both neutral and amino sugars and substantial amounts of galactose and sialic acid. The carbohydrate composition of EPO of the invention differs from the published carbohydrate composition of human urinary EPO. (We have not independently analyzed urinary EPO, and therefore cannot be certain the published results are accurate.) The rEPO of the invention was determined to have high biological activity in in vitro and in vivo assays.

Therapeutic Use

Human EPO can be lyophilized and reconstituted in steric water prior to use. EPO in saline can be administered on a regular basis (e.g., weekly) to human Patients suffering from anemia or renal failure. Administration is by the modes of administration used for other blood affecting proteins, e.g., tissue plasminogen activator. Most preferably, administration is by bolus injection or by intravenous infusion.

For long-term maintenance of a human patient, for example, 10–100 μg of lyophilized EPO are dissolved in sterile water and placed in the chamber of a syringe, which is used to inject a bolus of EPO into the patient intravenously; treatment is carried out three times per week.

Diagnostic use

Antibodies, either polyclonal or monoclonal, can be raised to EPO and used in conventional immunoassay methods to quantify EPO in biological fluids, e.g., serum or urine, of patients suspected of being deficient in EPO.

Deposits

E. coli cells containing the plasmid CES have been deposited with the Agricultural Research Culture Collection, and assigned NRRL Accession Number B-18113.

Applicants' assignee, Integrated Genetics, Inc., acknowledges its responsibility to replace this culture should it die before the end of the term of a patent issued hereon, 5 years after the last request for a culture, or 30 years from the date of deposit, whichever is the longer, and its responsibility to notify the depository of the issuance of such a patent, at which time the deposits will be made irrevocably available to the public. Until that time the deposit will be made available to the Commissioner of Patents under the terms of 37 CFR Section 1-14 and 35 USC Section 112.

Other embodiments are within the following claims. For example, although the use of all of the BPV genome is preferred, just the 69% transforming region can also be used. However, when only the 69% region is used, there might be undesirable interactions between the plasmid and the chromosome of the host cell, i.e., much of the plasmid DNA can incorporate into the chromosome rather than remaining episomal, so that the plasmid is more difficult to retrieve from the cells. Also, if less than the entire BPV genome is used, the pBR region which is frequently attached to BPV (since BPV is normally provided as part of a pBR322-derived plasmid), must be removed prior to transfection, because the pBR region, in a less than complete BPV fragment, can have an inhibitory effect on transfection. This does not occur when using full length BPV DNA. Undesirable rearrangements might also occur when using only the 69% region.

It is preferable that the eukaryotic metallothionein promoter be of mammalian, most preferably murine, origin, but any suitable metallothionein promoter can be used (each mammalian species which produces a metallothionein apparently does so using a structurally different gene).

To construct a vector within the invention, other than CES, cell line DNA can be used as the source of the MT promoter and structural gene, the EPO gene, and the BPV genome, and those genetic elements can be inserted, using conventional recombinant DNA techniques, into a desired vector.

Any suitable host cells can be used. For example, other rodent fibroblast cell lines which can be infected by BPV can be used; for example, NIH 3T3 cells (ATCC CCL 92) can be used.

We claim:
1. A C127 cell transformed with a recombinant DNA vector comprising a DNA sequence encoding human erythropoietin, said transformed cell being capable of producing N-linked and O-linked glycosylated human erythropoietin.
2. The cell of claim 1 wherein said DNA sequence encoding human erythropoietin is under the transcrip- tional control of a promoter for a eukaryotic metallothionein gene.

3. The cell of claim 2 wherein said vector further comprises at least the 69% transforming region of the bovine papilloma virus genome.

4. The cell of claim 1, said cell being a mouse C127 cell.

5. A method of producing at least 99% pure EPOP, said method comprising
   (a) culturing C127 cells transformed with a recombinant DNA vector encoding human EPO in nutrient medium free of serum to produce EPO-containing medium,
   (b) clarifying said medium of cell debris to yield clarified EPO-containing medium,
   (c) subjecting said EPO-containing medium to ion exchange chromatography to yield partially purified EPO,
   (d) subjecting said partially purified EPO to reverse phase HPLc in an organic solvent to yield pure EPO in said organic solvent, and
   (e) removing said organic solvent.

6. The method of claim 5 wherein said step (e) is carried out by ion exchange chromatography.

7. The method of claim 5 wherein said step (e) is carried out by solvent evaporation of removal by dialysis, followed by gel filtration.

8. The method of claim 5 wherein, following said step (b), said clarified EPO-containing medium is treated to inhibit proteolytic degradation of said EPO during said step (c).

9. The method of claim 8 wherein said treatment to inhibit proteolytic cleavage comprises removal of proteases in said clarified EPO-containing medium by fractionation on a dye column.

10. The method of claim 8 wherein said treatment to inhibit proteolytic cleavage comprises addition to said clarified EPO-containing medium of a protease inhibitor.

* * * * *

UNITED STATES PATENT AND TRADEMARK OFFICE
CERTIFICATE OF CORRECTION

PATENT NO. : 4,954,437

DATED : September 4, 1990

INVENTOR(S) : Beck et al.

It is certified that error appears in the above—identified patent and that said Letters Patent is hereby corrected as shown below:

1. Add to the list of inventors: --Henry Hoppe, IV, Acton, Massachusetts--.

2. Claim 5, line 10, delete "EPOP" and substitute therefor --EPO--.

Signed and Sealed this

Twenty-eighth Day of April, 1992

Attest:

HARRY F. MANBECK, JR.

Attesting Officer

Commissioner of Patents and Trademarks